United States Patent [19]

Chu

[11] Patent Number: 4,702,266
[45] Date of Patent: Oct. 27, 1987

[54] DESTAINING APPARATUS FOR ELECTROPHORESIS GELS

[75] Inventor: Daniel Y. M. Chu, San Francisco, Calif.

[73] Assignee: Bio-Rad Laboratories, Inc., Richmond, Calif.

[21] Appl. No.: 871,058

[22] Filed: Jun. 5, 1986

Related U.S. Application Data

[62] Division of Ser. No. 653,393, Sep. 20, 1987.

[51] Int. Cl.$^4$ .............................................. B08B 3/02
[52] U.S. Cl. ..................................... 134/60; 134/92; 204/299 R; 206/509
[58] Field of Search ...................... 134/2, 34, 60, 111, 134/182, 183, 84, 92, 184, 195, 201; 204/108 G, 182.8, 299 R; 206/501, 509, 511, 519, 512, 518, 520; 354/331, 337

[56] References Cited

U.S. PATENT DOCUMENTS

| | | | |
|---|---|---|---|
| 335,002 | 1/1886 | Whiting | 354/337 |
| 1,947,055 | 2/1934 | Moorman | 206/511 |
| 2,141,162 | 12/1938 | Brandt | 134/118 |
| 2,765,913 | 10/1956 | Weiss et al. | 134/60 X |
| 3,118,829 | 1/1964 | Raymond | 204/299 R |
| 3,317,418 | 5/1967 | Zec | 204/299 R |
| 3,341,064 | 9/1967 | Ricci | 206/512 |
| 3,450,624 | 6/1969 | Natelson | 204/299 R |
| 3,494,846 | 2/1970 | Arquembourg | 204/299 X |
| 3,499,833 | 3/1970 | Ferris et al. | 204/182.8 X |
| 3,888,159 | 6/1975 | Elson et al. | 204/182.8 X |
| 4,284,491 | 8/1981 | Vesterberg | 204/182.8 X |
| 4,310,408 | 1/1982 | Rose et al. | 204/299 R X |
| 4,373,633 | 2/1983 | Lutz, Sr. | 206/509 X |

FOREIGN PATENT DOCUMENTS

| | | | |
|---|---|---|---|
| 146082 | 10/1901 | Fed. Rep. of Germany | 354/337 |
| 276924 | 8/1913 | Fed. Rep. of Germany | 354/337 |
| 475471 | 6/1926 | Fed. Rep. of Germany | 354/337 |
| 2356178 | 5/1975 | Fed. Rep. of Germany | 204/180 G |

*Primary Examiner*—Harvey C. Hornsby
*Assistant Examiner*—Frankie L. Stinson
*Attorney, Agent, or Firm*—Townsend & Townsend

[57] ABSTRACT

A multiple gel destaining apparatus is disclosed, in which the gels are laid out horizontally in a series of trays arranged in a stack. Ech tray accomodates either one slab gel or one layer of tube gels. The trays are of interchangeable construction, and designed with appropriately placed openings for fluid passage so that destaining fluid flows through the tray stack in a serpentine path, sweeping one tray then sweeping the next in the opposited direction. The tray stack is submerged in a tank with continuous circulation of destaining fluid, arranged to draw the fluid downward through the stack, outward through a filter at the bottom of the tank, and upward along the sides of the tank to the top of the stack.

11 Claims, 4 Drawing Figures

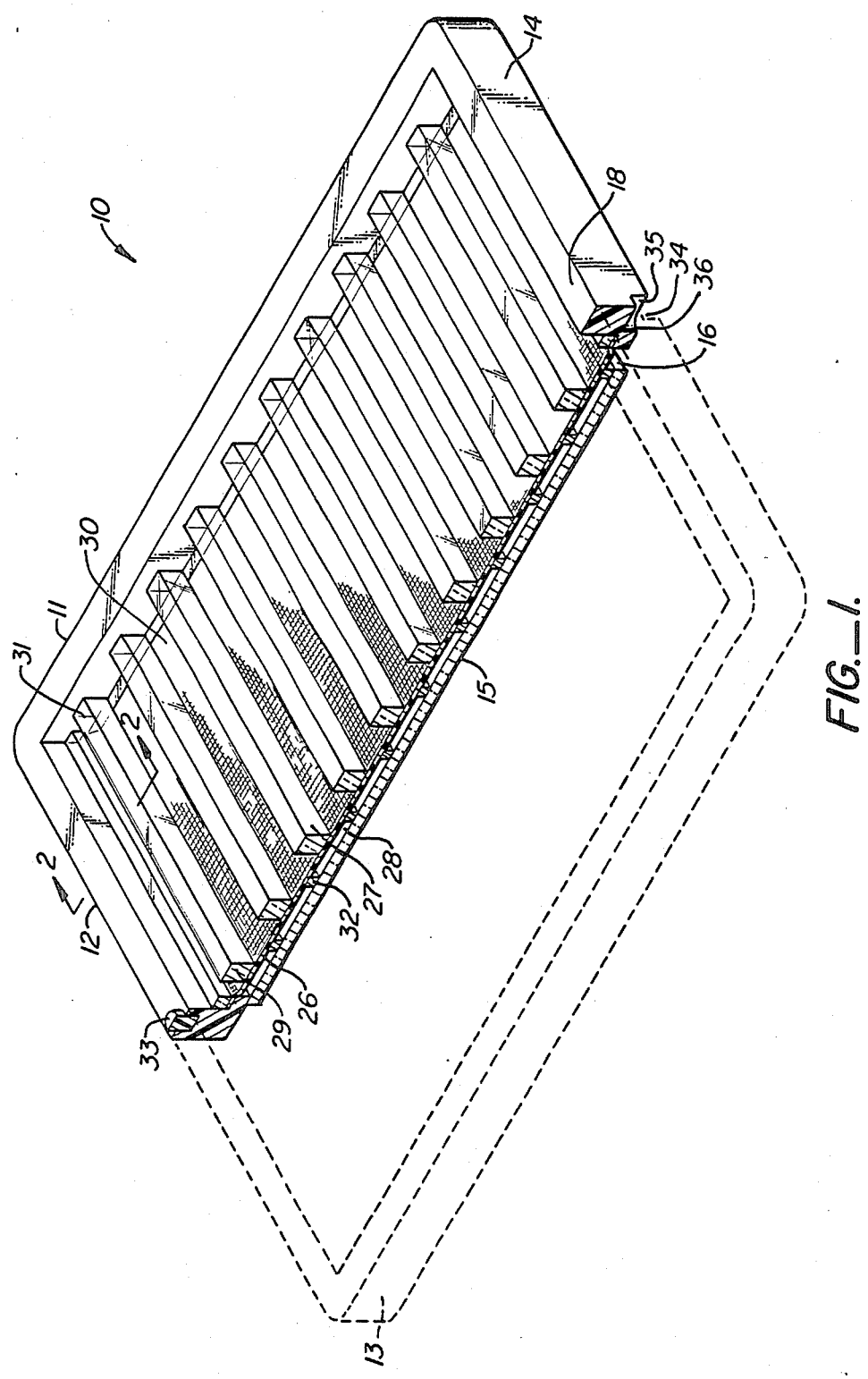
FIG._1.

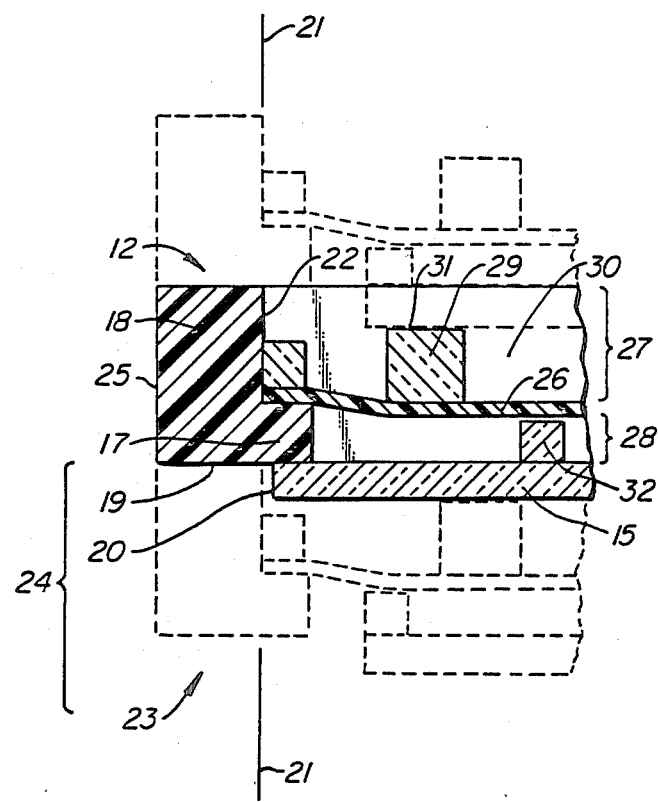
FIG._2.

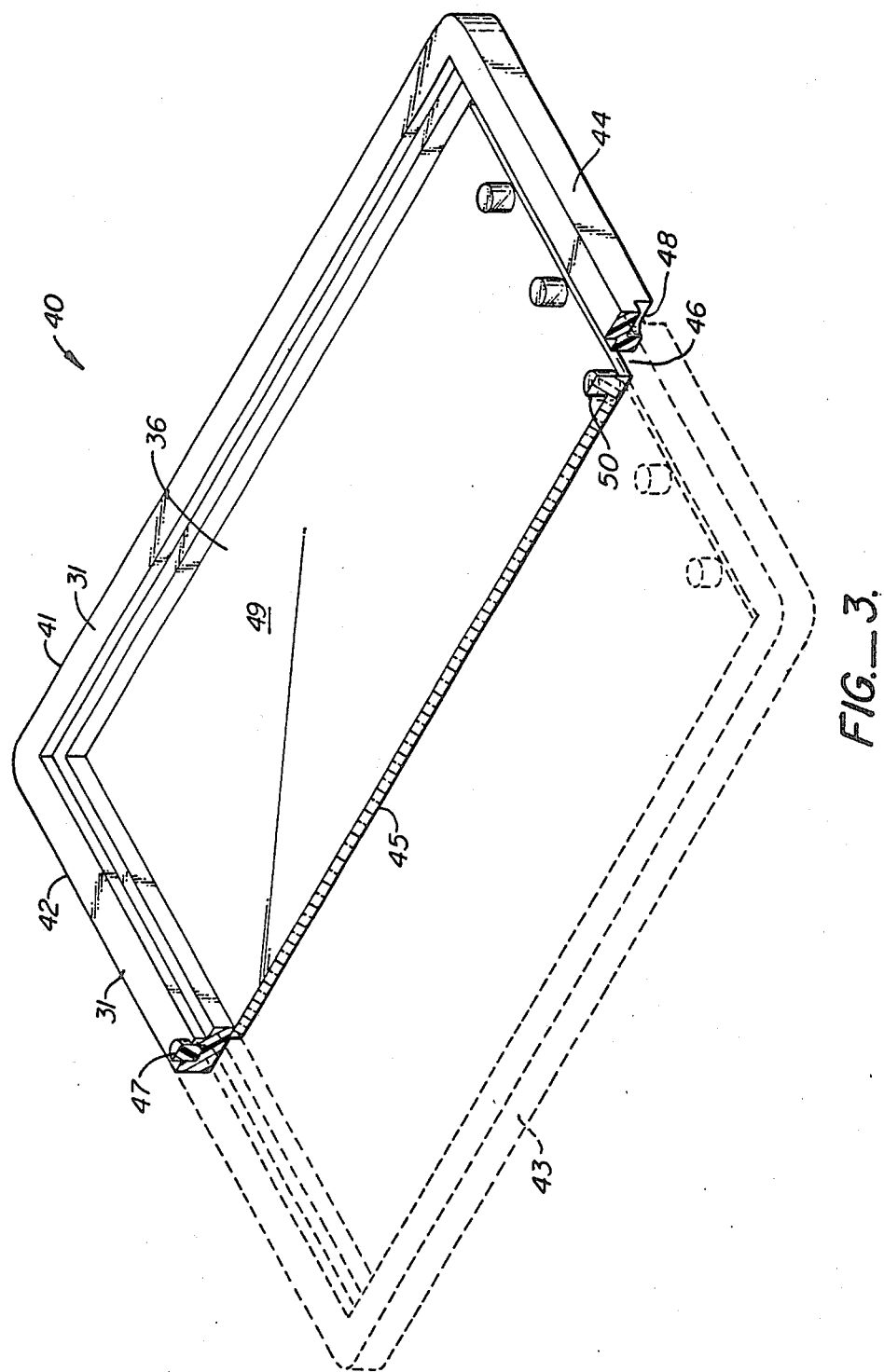
FIG._3.

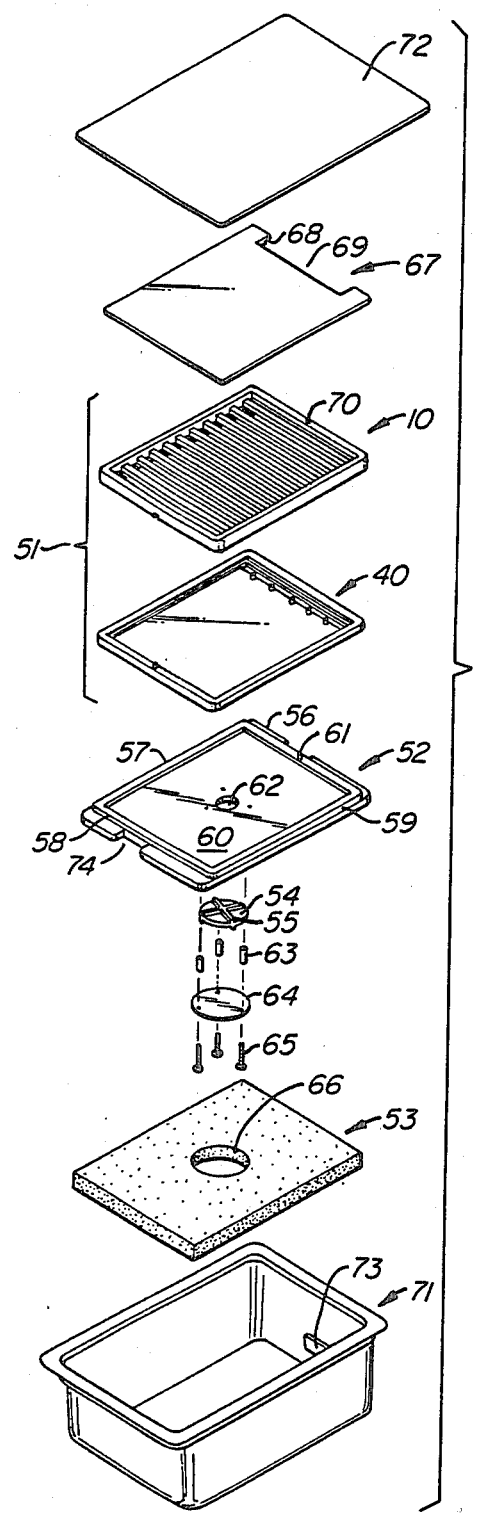
FIG._4.

4,702,266

DESTAINING APPARATUS FOR ELECTROPHORESIS GELS

This is a division of application Ser. No. 653,393 filed Sept. 20, 1984, pending.

BACKGROUND OF THE INVENTION

This invention relates to the removal of background stain in electrophoresis gels by diffusion destaining. In particular, this invention relates to apparatus for the simultaneous destaining of a multitude of gels, both tube-shaped and slabs, in a continuously circulating destaining fluid.

In diffusion destaining, maximum contact is sought between the gel and a flowing diffusion fluid. When destaining several gels simultaneously, this generally requires a large flow rate of diffusion fluid, particularly when one seeks to provide the same degree of access of the fluid to all gels. When the principles of existing destainer designs are applied, this entails the use of a large physical space for the destainer and a high pumping capacity to circulate the fluid.

SUMMARY OF THE INVENTION

The present invention resides in a novel gel destaining apparatus and method in which the gels are laid on a series of trays with one gel layer per tray, the trays are joined together with the gels in between, and destaining fluid is passed across each tray in succession, sweeping the trays in alternating directions. Destaining fluid drawn through the joined trays thus follows a sweeping flow path along each tray rather than transverse flow. By providing successive contact of the gels with a relatively small amount of destaining fluid, the invention permits thorough circulation of the fluid through a large number of gels in a compact space, requiring only moderate pumping capacity.

Each tray is designed to promote a high and uniform degree of access of the fluid to each gel, and yet to maintain inter-tray openings clear for unobstructed fluid passage. Thus, each tray has sides sufficiently raised to accommodate a single gel layer, and an opening in the base along the length of one side. In preferred embodiments, the raised sides have design features to facilitate stacking.

The internal construction of a tray is variable depending on whether it is intended for tube gels or a slab gel. The stacking features and inter-tray openings are uniform, however, rendering the trays interchangeable in the stack. As a result, any number of tube gels, slab gels or both may be accommodated without substantial fluid by-pass.

In use, the tray stack is submerged in a destaining fluid held in a circulation tank. A fluid circulation device is placed in the tank at one end of the stack to draw the fluid through the stack, causing the fluid to follow the serpentine tray-sweeping flow path described above along the entire length of the stack. The stain-bearing fluid flowing out the tray at one end of the stack is passed through a stain-removing filter, then back over the outside of the stack to the other end for re-entry. The entire apparatus is readily assembled and disassembled with no adjustments required other than the formation of the stack itself.

BRIEF DESCRIPTION OF THE DRAWINGS

FIG. 1 is a sectional perspective view of an illustrative stacking tray according to the present invention, for the destaining of tube gels.

FIG. 2 is a sectional view of one side of the stacking tray depicted in FIG. 1, taken along the line 2—2 of FIG. 1.

FIG. 3 is a sectional perspective view of an illustrative stacking tray according to the present invention, for the destaining of a slab gel.

FIG. 4 is an exploded perspective view of an illustrative destaining apparatus, including a stack of the trays of FIGS. 1 and 3, together with a tank, filter and fluid circulation device and associated components.

DESCRIPTION OF THE PREFERRED EMBODIMENTS

The overall operation of the destaining apparatus may be understood by first examining the individual stacking trays, each of which is preferably designed for gels of a single type.

FIG. 1 depicts an exemplary stacking tray 10 for tube gels. The tray is constructed of four raised sides 11, 12, 13 and 14 and a base 15 which partially encloses the bottom of the tray leaving an elongate narrow opening 16 extending the full length of one side 14. These features are common to both the tube gel tray and the slab gel tray. In preferred embodiments, these features are of interlocking shape to promote a close and stable stacking arrangement. A detailed depiction of such features appears in FIG. 2.

FIG. 2 is a vertical cross-section of one side 12 of the tray shown in FIG. 1. It will be noted that the cross-section is in the shape of an upright L opening inward, with a horizontal portion 17 and a vertical portion 18. The base 15 of the tray is a flat rectangular plate secured to the bottom surface 19 of the horizontal portion 17 of the L. The base plate 15 is not coextensive with the sides but rather terminates short of each side to which it is secured, such that its outer edge 20 terminates inside the plane 21 defined by the inner surface 22 of the vertical portion 18 of the L (i.e., to the right of the plane, in the view shown in FIG. 2). The base plate 15 of one tray thus fits inside the raised sides 23 of the next lower tray, thus permitting the trays to be stacked in a close-fitting stable manner with their sides in vertical alignment and without lateral slippage. The corresponding sides 12 and 23 of adjacent trays 10 and 24 in the stack abut one another, forming a column enclosed at the sides by a continuous wall 25. It will further be noted in this figure that the trays are stacked in alternating directions, as explained below.

As also shown below, the sides and base of the slab gel tray are similarly shaped, to promote an interlocking stacking arrangement with either type of tray.

Returning to FIG. 1 and the features specifically adapted for use with tube gels, a gel-supporting partition 26 is secured horizontally across the interior space of the tray, parallel to the base plate 15, and dividing the interior space into upper and lower portions 27 and 28. The partition 26 is of any structure capable of passing the flow of destaining fluid, and sufficiently taut or rigid to support a layer of tube gels. A convenient structure for the partition is that of a large mesh screen.

The space above the screen contains a series of vertical partitions 29 of non-fluid-penetrable construction, extending across the width of the tray. These partitions divide the upper portion of the tray into a series of parallel troughs 30, each parallel to the opening 16 in base plate 15 and sized to accommodate approximately one tube gel. The dimensions of the troughs may be varied as desired to accommodate tube gels of various diameters and lengths. A typical construction may involve troughs approximately 0.6 inch (1.5 cm) in width, 0.25 inch (0.6 cm) deep, and 6.5 inches (16.5 cm) long.

In the embodiment shown in the drawings, the upper edge 31 of each vertical partition 29 is at a level below the height of the raised sides 11-14, the difference in height being approximately equal to the thickness of the base plate 15. When the trays are stacked as described above, the base plate 15 of one tray will thus rest on or be slightly above the top edges 31 of the partitions 29 of the next lower tray, closing off the troughs 30 in the lower tray with the tube gels inside.

Between the partition screen 26 and the base plate 15 are a series of baffles 32 extending across the width of the tray, parallel to and staggered with the vertical partitions 29 in the upper portion of the tray interior. The arrangement of partitions and baffles serves to direct the fluid flow toward and around each tube gel to sweep the entire circumference of the gel, avoiding the crowding of gels and preventing the fluid from bypassing the gels. When the trays are stacked and the troughs 30 closed off as described above, a fluid flow path of undulating cross-section is formed. With the trays stacked so that the base plate openings 16 are at alternating sides, the fluid enters the interior space of the tray from above near side 12, passing through the first trough (which is left open), down through the partition screen 26, underneath the first vertical partition 29, back up through the screen and around the first gel (flowing in the direction transverse to the gel axis), then back down through the screen and underneath the second partition, then back up around the second gel, etc., until finally exiting downward through the base plate opening 16 which is located at the side opposite the side of entry. The fluid then follows an identical flow path, although in the reverse direction, across the next lower tray.

To ensure proper stacking of the trays with the alternating placement of the base plate openings 16, a guide pin 33 projects upward from the top of one side of the tray, and a corresponding indentation 34 is located in the bottom of the opposite side, as shown. The trays are then stacked so that the pin of one tray rests inside the indentation of an adjacent tray.

In the embodiment shown in FIG. 1, the indentation is an inverted groove which runs perpendicular to the direction of the side in which it is formed. The groove is open at its outward end 35 and closed or truncated at its inner end 36. This permits the sliding entry of the guide pin 33 from the lower tray into the groove from the outer end 35, yet stops the trays from sliding further with respect to each other once the base plate of the upper tray and the raised sides of the lower tray are engaged. Accordingly, the elongate opening 16 at the base of each tray is kept open, and vertical alignment of the sides is maintained.

The guide pin and indentation features are common to both the tube gel and slab gel tray structures, as are the interlocking features described above. This will become evident from the description of FIG. 3 which follows, further promoting the interchangeability of the trays.

FIG. 3 depicts an exemplary stacking tray 40 for a slab gel. This tray contains the common features described above, namely: four raised sides 41, 42, 43, and 44, a base plate 45 leaving an elongate narrow opening 46 extending the full length of one side 44, a guide pin 47 projecting up from the top of one side 42, and an inverted truncated groove 48 in the bottom of the opposing side 44. The slab gel rests directly on the upper surface 49 of the base plate 45, and is retained in place by at least one or a row of pins 50 which protrude upward from the plate along the edge adjacent the base plate opening 46. These pins prevent the slab from drifting into the opening under the influence of the fluid flow, where the slab might become damaged or block the flow. The pins are widely enough spaced, however, such that they offer substantially no obstruction to the fluid flow itself.

The frame sides are of L-shaped cross-section as in the tube gel tray depicted in FIGS. 1 and 2, thus permitting close and stable stacking and preventing lateral slippage of the trays in the stack in the manner described above. The guide pin 47 and truncated groove 48 further stabilize the stacking in the same manner as the corresponding guide pin 33 and groove 34 in the tube gel tray, while ensuring alternating placement of the base plate openings in the stacked trays and maintaining an open passage through the openings.

Due to their similarity of construction, trays of both types may be stacked in any arrangement or combination. Thus, regardless of which trays are used, how many, and in which order, the fluid flow path will sweep each tray in alternate directions as it proceeds downward through the stack, providing each gel, whether tube or slab, full contact with the circulating diffusion fluid. The term "stack" is used herein to denote two or more trays of any combination combined top to bottom with a one layer of gels in between each adjacent pair of trays. In the preferred practice of the invention, the stack is arranged as a vertical column.

A simplified stacking arrangement with accessory parts is shown in an exploded view in FIG. 4.

A simple stack 51 consisting of the tube gel tray 10 of FIG. 1 and the slab gel tray 40 of FIG. 3 is shown, although as stated above an entire stack of one or the other or any combination may be substituted.

Beneath the stack is a support structure 52 which guides the destaining fluid leaving the lowest tray of the stack through a filter 53 which extracts the stain so that clean fluid may circulate back up to the top of the stack. In the example shown in the drawing, the fluid circulation is driven by a rotating disk 54 with radial blades 55 acting as a vortex pump at the base of the stack.

The support structure 52 is designed so that the vortex draws fluid only from the interior passages of the tray stack. Thus, the structure contains four raised sides 56, 57, 58 and 59 and a base plate 60, as well as a pin 61 protruding upward from one side, similar to those of the stacking trays. The sides and base plate thus form a chamber beneath the bottom plate of the lowest tray of the stack 51. It will be noted that the bottom plate of the lowest tray in the stack fits inside the raised sides 56, 57, 58 and 59 of the support structure, and the pin 61 in the support structure mates with an indentation or groove in the bottom of one side of the lowest tray (not shown), both in the same manner as between adjacent trays at other locations in the stack. The chamber thus formed surrounds the opening in the lowest tray, and the pin prevents the tray from sliding sideways to obstruct the opening. Accordingly, all fluid from the lowest tray is drawn into the chamber and out through the orifice 62 in the center of the support structure base plate 60.

The rotating disk 54 is loosely retained below the orifice 62 at the bottom of the support structure by an enclosure formed by spacers 63 and a support disk 64. Screws 65 passing through the support disk and spacers secure these parts to the support structure. The torque on the rotating disk is provided by a rotating magnetic field which interacts with a magnet embedded in the disk. The rotating magnetic field may be provided by any conventional magnetic stirring apparatus such as those commonly used in chemical laboratories. Accordingly, the entire destaining apparatus is conveniently placed on top of a magnetic stirring plate.

The filter 53 is in the shape of a flat pad having a central hole 66. The filter is placed beneath the support structure, with the disk enclosure passing through the hole 66. The centrifugal force of the rotating disk blades 55 forces the fluid leaving the orifice 62 to pass through the filter. The filter may consist of any conventional inert material which is capable of extracting electrophoresis gel stain from the destaining fluid. A typical material is foam rubber impregnated with activated carbon.

Above the stack is a cover plate 67 having an inverted ledge 68 around the perimeter as shown, and a long notch 69 at one side. The ledge 68 permits a snug fit of the cover plate inside the raised sides of the top tray of the stack 51, thus enclosing the interior space of the tray while the notch 69 leaves a narrow opening at one side. The pin 70 protruding upward from the top tray in the stack permits placement of the cover plate in only one direction, ensuring that the narrow opening in the cover plate will continue the alternating pattern established by the base plate openings throughout the height of the stack.

The remainder of the apparatus includes a tank 71 to hold destaining fluid and sized to accommodate the entire tray stack 51 plus the support structure 52, filter 53 and cover plate 67, all submerged beneath the liquid level. A protective lid 72 fits over the tank.

Since the filter may be buoyant, the support structure is preferably held down by tabs 73 affixed to the inside of the tank to overlap the extended side edges of the base plate 60 of the support structure 52. For insertion and removal of the support structure, the base plate 60 contains offset notches 74 on its rim, to mate with the tabs 73. The amount of offset is selected so that the loose fit of the support structure inside the tank will permit one to slide the support structure along the length of the notches for engagement and disengagement of the tabs.

When the entire apparatus shown in FIG. 4 is assembled, the tank filled with destaining fluid and the magnetic disk rotating, the fluid will enter the stack 51 through the notch 69 in the cover plate 68, flow downward through the stack, sweeping each tray in succession and in alternating directions, pass through the orifice 62 in the support structure 52, be directed outward by the disk blades 55 through the filter 53 (at the base of the tank) where dye will be absorbed, and pass up the walls of the tank 71 to the top where it will re-enter the notch 69 in the cover plate 68.

The materials of construction of the apparatus are not critical. Any conventional inert materials, preferably those suitable for machining, extrusion, injection molding or other common means of manufacture, may be used. It is further preferred that the parts of the apparatus which vertically overlap the gels, such as the base plates, trough partitions, baffles and cover plate be transparent so that the progress of the stain removal can be monitored visually by the operator. Acrylic plastics, both clear and opaque, are particularly useful.

The apparatus of the present invention is intended for use with conventional gels such as polyacrylamide gels, and conventional diffusion destaining fluids such as aqueous acetic acid solution.

The foregoing description is offered primarily for illustrative purposes. It will be readily apparent to those skilled in the art that numerous modifications in variations of the materials and the components and their configurations as disclosed above may be introduced without departing from the spirit and scope of the invention, as set forth in the appended claims.

What is claimed is

1. A stacking tray for supporting at least one electrophoresis gel in a body of flowing destaining fluid, said tray comprising four sides and a base having an elongate opening in said base adjacent to one of said sides, said sides being raised sufficiently to leave an interior space sufficient to accommodate said gel when said tray is combined with further said trays in a stack, said tray further comprising a pin projecting upward from the top of one of said raised sides and an indentation in the bottom of the opposing side to receive another said pin projecting upward from the next lower tray in said stack such that said pin provides means for the preventing the stacking of said tray in any manner except that in which said elongate openings in all adjacent pairs of trays in said stack are opposite sides.

2. A stacking tray in accordance with claim 1 further comprising means for interlocking said tray with adjacent said trays above and below it in said stack to substantially prevent lateral slippage.

3. A stacking tray in accordance with claim in which said base is transparent.

4. A stacking tray in accordance with claim 1 in which each said side is of upright L-shaped cross-section opening inward, and said base is comprised of a rectangular flat plate secured to the bottom surface of the horizontal portion of said L along three of said sides, each edge of said plate terminating on the inner side of the plane defined by the inner surface of the vertical portion of said L, such that said plate fits inside the raised sides of the next lower tray in said stack.

5. A stacking tray in accordance with claim 1 further comprising means for retaining said gel in said tray and clear of said opening without substantially obstructing fluid flow along said base toward said opening.

6. A stacking tray in accordance with claim 1 in which said indentation is an inverted groove running perpendicular to said opposing side, the inward end of said groove being truncated to limit the position therein of said pin of said next lower tray.

7. A stacking tray for supporting at least one electrophoresis gel in a body of flowing destaining fluid, said tray comprising:

four sides and a base having an elongate opening in said base adjacent to one of said sides, said sides being raised sufficiently to leave an interior space sufficient to accommodate said gel when said tray is combined with further said trays in a stack;

means for preventing the stacking of said tray in any manner except that in which said elongate openings in all adjacent pairs of trays in said stack are at opposite sides;

a gel-supporting horizontal partition penetrable by said fluid, dividing the interior of said tray into upper and lower portions;

a plurality of non-penetrable vertical partitions in said upper portion dividing said upper portion into a plurality of troughs parallel to said elongate openings, each trough sized to receive approximately one tube gel; and a plurality of baffles in said lower portion parallel to and in staggered relation with said vertical partitions to define an undulated fluid flow path passing around said tube gels.

8. A stacking tray for supporting a plurality of tube gels in a flowing stream of destaining fluid, said tray comprising:

four raised sides and a base in the form of a flat plate secured to the bottom edges of three of said sides, leaving an elongate opening in said base adjacent to said fourth side;

a gel-supporting horizontal partition penetrable by said fluid, dividing the interior of said tray into upper and lower portions;

a plurality of non-penetrable vertical partitions dividing said upper portion into a plurality of troughs parallel to said elongate opening, each trough sized to accommodate approximately one tube gel; and a plurality of baffles in said lower portion parallel to and in staggered relation with said vertical partitions to define an undulated fluid flow path passing around said tube gels;

said tray being combinable with further said trays in a stack in which said raised sides form a continuous wall, the flat plate of one said tray rests on the upper edges of said vertical partitions of the next lower tray, and said elongate openings of all adjacent pairs of trays in said stack are at opposite sides.

9. A stacking tray in accordance with claim 8 in which said flat plate, said vertical partitions and said baffles are transparent.

10. A tray for supporting a plurality of tube gels in a flowing stream of destaining fluid, and for combining with additional said trays in a stack, said tray comprising:

a base and four raised sides, each side being of upright L-shaped cross-section opening inward and said base comprising a flat rectangular transparent plate secured to the bottom surface of the horizontal portion of said L along three of said sides leaving an elongate opening along said fourth side, each edge of said plate terminating on the inner side of the plane defined by the inner surface of the vertical portion of said L, such that said plate fits inside the raised sides of the next lower tray in said stack, with said sides of adjacent trays in said stack abutting to form a continuous wall;

a gel-supporting horizontal partition penetrable by said fluid, dividing the interior of said tray into upper and lower portions;

a plurality of non-penetrable vertical transparent partitions dividing said upper portion into a plurality of troughs parallel to said elongate opening, each trough sized to receive approximately one tube gel;

a plurality of transparent baffles in said lower portion parallel to and in staggered relation with said vertical partitions to define an undulated fluid flow path passing through said tube gels;

a pin projecting upward from the top of one of said raised sides; and an inverted groove in the bottom of the side opposing the side bearing said pin, said groove running perpendicular to said opposing side and the inward end of said groove being truncated to limit the position therein of said pin of the next lower tray in said stack.

11. A tray for supporting a slab gel in a flowing stream of destaining fluid and for combining with additional said trays in a stack, said tray comprising:

a base and four raised sides, each side being of upright L-shaped cross-section opening inward and said base comprising a flat rectangular transparent plate secured to the bottom surface of the horizontal portion of said L along three of said sides leaving an elongate opening along said fourth side, each edge of said plate terminating on the inner side of the plane defined by the inner surface of the vertical portion of said L, such that said plate fits inside the raised sides of the next lower tray in said stack, with said sides of adjacent trays in said stack abutting to form a continuous wall;

at least one retaining pin protruding upward from said base adjacent to said elongate opening to retain said gel slab on said base clear of said elongate opening;

a guide pin projecting upward from the top of one of said raised sides;

an inverted groove in the bottom of the side opposing the side bearing said guide pin, said groove running perpendicular to said opposing side and the inward end of said groove being truncated to limit the position therein of said guide pin of said next lower tray.

* * * * *